United States Patent [19]

Chorvat et al.

[11] Patent Number: 4,704,382

[45] Date of Patent: Nov. 3, 1987

[54] PHENYLPIPERAZINE PHOSPHONATES

[75] Inventors: Robert J. Chorvat, Lake Bluff; Kerry W. Fowler, Chicago; James P. Snyder, Glenview, all of Ill.

[73] Assignee: G. D. Searle & Co., Chicago, Ill.

[21] Appl. No.: 880,560

[22] Filed: Jul. 8, 1986

Related U.S. Application Data

[63] Continuation-in-part of Ser. No. 760,230, Jul. 29, 1985, abandoned.

[51] Int. Cl.$^4$ ................ A61K 31/495; C07D 295/08; C07D 295/10
[52] U.S. Cl. ........................................ 514/85; 544/337
[58] Field of Search ........................... 544/337; 514/85

[56] References Cited

FOREIGN PATENT DOCUMENTS 76996 10/1981 European Pat. Off. .

OTHER PUBLICATIONS

Tsuda, et al., Chem. Abstracts, vol. 106, (1987), entry 67489s.
J. H. Sanner & C. M. Prusa, "Inhibition by Verapamil of Contractions Produced by Calcium and Depolarized Rabbit Aortic Strips", *Life Sciences,* 27, 2565–2570, (1980).
J. M. Van Rossum, "Cumulative Dose Response Curves, II . . . ," *Arch. Int. Pharmacodyn.,* 143, 299–330, (1963).

*Primary Examiner*—Donald G. Daus
*Assistant Examiner*—William A. Teol, Jr.
*Attorney, Agent, or Firm*—J. Timothy Keane; Paul D. Matukaitis

[57] ABSTRACT

The invention relates to compounds of the formula:

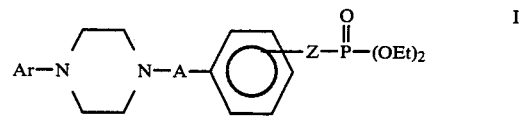

which are useful cardiovascular agents.

19 Claims, No Drawings

PHENYLPIPERAZINE PHOSPHONATES

BACKGROUND OF THE INVENTION

This application is a continuation-in-part of application Ser. No. 760,230 filed July 29, 1985 now abandoned. The present invention provides novel compounds of formula I

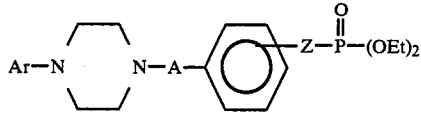

which are pharmacologically useful as cardiovascular agents. More specifically, the compounds of the present invention are orally active antihypertensive agents which promote their blood pressure lowering effects through both calcium ion antagonism and alpha adrenoceptor blockade.

The present invention also relates to novel pharmaceutical compositions comprising one or more of the active compounds of the invention in combination with suitable pharmaceutical carriers as well as methods of using such compounds and pharmaceutical compositions thereof in the treatment, prevention, or mitigation of cardiovascular diseases or conditions, including specifically acute and chronic hypertension.

PRIOR ART

European Pat. No. 76,996 discloses compounds of the formula

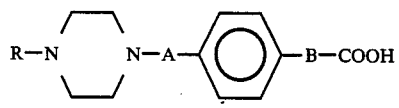

wherein A is a bond or lower alkylene; B is a bond or optionally unsaturated lower alkylene; R is H, alkyl (or optionally substituted alkyl), aralkyl, aryl, acyl or phenacyl, etc. provided that when A is a bond, R is not H, methyl, ethyl, hydroxyethyl, benzyl or phenyl. The foregoing compounds are structurally unrelated to the phosphonic acid esters of the present invention. Moreover, the carboxylic esters of the above art are disclosed as having only lipid-reducing activity and thrombocyte aggregation inhibition activity and thus have pharmacological properties by reason of their different chemical structure which are distinguishable from the antihypertensive compounds of the present invention.

SUMMARY OF THE INVENTION

The present invention provides compounds of the general formula I:

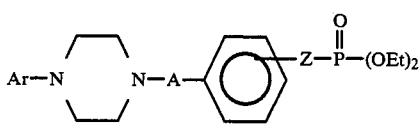

and the pharmaceutically acceptable salts thereof; wherein Ar is a pyridyl group or a

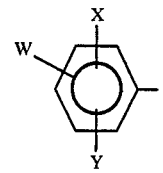

group, wherein X, Y and W are the same or different and independently selected from hydrogren, $C_1$-$C_4$ alkoxy, $C_1$-$C_6$ alkyl or halogen; wherein A represents —$CH_2$—,

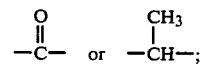

and wherein Z represents a bond or —$CH_2$— or

The compounds and pharmaceutical compositions thereof are useful in the cardiovascular methods of the invention.

DETAILED DESCRIPTION OF THE INVENTION

The compounds of the present invention comprise those of formula I:

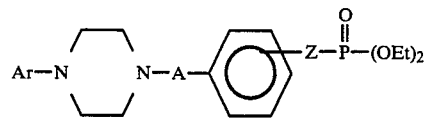

and the pharmaceutically acceptable salts thereof; wherein Ar is a pyridyl group or a

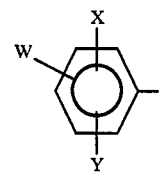

group, wherein X, Y and W are the same or different and independently selected from hydrogen, $C_1$-$C_4$ alkoxy, $C_1$-$C_6$ alkyl or halogen; wherein A represents —$CH_2$—,

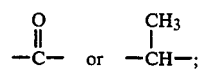

and wherein Z represents a bond or —$CH_2$— or

As used herein, the expressions "alkyl" and "alkoxy" are defined to include straight or branched carbon-carbon linkages having the number of carbon atoms indicated. Representative alkyl moieties of either group include methyl, ethyl, propyl, butyl, pentyl, sec-butyl, etc. and the corresponding other isomeric forms thereof.

The term "halogen" includes bromine, chlorine, and fluorine with chlorine and fluorine being especially preferred.

The compounds herein may also be prepared as addition salt forms thereof and such forms are included in the present compound formulas. Typical of such "pharmaceutically acceptable salts" are those derived from mineral or organic acids including, for example, hydrochloric, hydrobromic, hydroiodic, sulfuric, nitric, acetic, oxalic, citric, maleic, succinic, and the like.

—CH$_2$—; and the pharmaceutically acceptable salts thereof.

In the most preferred embodiments of the present invention the phosphonate ester moiety is in the para position on the phenyl ring and the substituents corresponding to X, Y or W are in the ortho or para position on the phenyl ring to which they are attached.

The compounds of the invention are facilely prepared according to one of the following reaction schemes or modifications thereof utilizing readily available starting materials, reagents and conventional synthesis procedures.

Scheme I

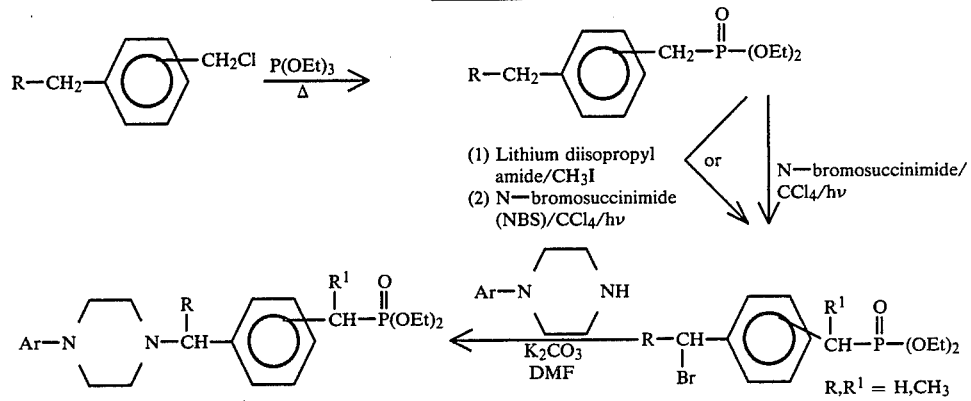

Scheme II

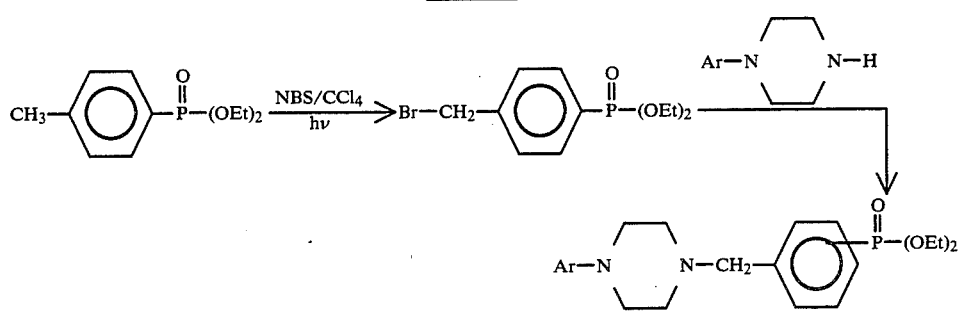

Scheme III

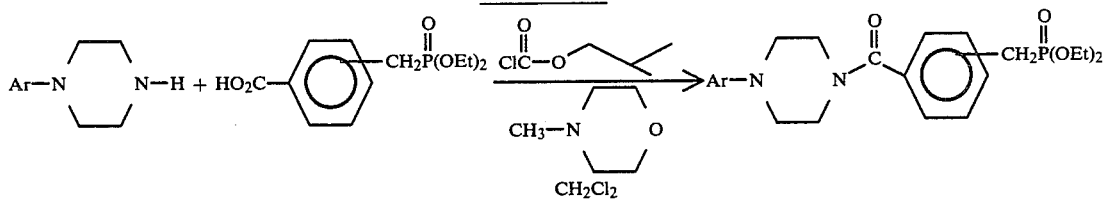

Representative of especially preferred compounds in accordance with the present invention are those wherein Ar is a

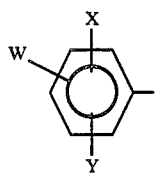

group wherein one of X, Y and W is methyl or methoxy and the others are hydrogen; and A and Z are both The compounds of the present invention can be administered in such oral dosage forms as tablets, capsules, pills, powders, granules, elixirs, or syrups. Likewise, they may also be administered intravascularly, intraperitoneally, subcutaneously, or intramuscularly using forms known to those of ordinary skill in the pharmaceutical arts. In general, the preferred form of administration is oral. An effective but non-toxic amount of the compound is employed in the treatment of hypertension or to promote calcium antagonism, etc. with resultant cardiovascular improvement. The dosage regimen utilizing the compounds of the present invention is selected in accordance with a variety of factors including the type, age, weight, sex, and medical condition of the patient; the severity of the condition to be ameliorated;

the route of administration; and the particular compound employed or mixtures thereof. An ordinarily skilled physician can readily determine and prescribe the effective amount of the drug required to prevent, treat or arrest the progress of the condition. Dosages of the compounds of the present invention, when used for the indicated cardiovascular effects, e.g., antihypertensive, will range between about 0.1 mg/kg/day to about 50 mg/kg/day. The foregoing dosage ranges on a weight basis correspond to a total daily dosage in the average adult patient of between about 10 mg/day to 350 mg/day. Advantageously, the compounds of the present invention may be administered in a single daily dose or the total daily dosage may be administered in equal divided doses three or four times daily.

In the pharmaceutical compositions and methods of the present invention, the foregoing active ingredients will typically be administered in admixture with suitable pharmaceutical diluents, excipients, or carriers (collectively referred to herein as "carrier" materials) suitably selected with respect to the intended form of administration, that is, oral tablets, capsules, elixirs, syrups, and the like, and consistent with conventional pharmaceutical practices. For instance, for oral administration in the form of tablets or capsules, the active drug components may be combined with any oral non-toxic pharmaceutically acceptable inert carrier such as lactose, starch, sucrose, cellulose, magnesium stearate, dicalcium phosphate, calcium sulfate, mannitol and the like; for oral administration in liquid form, the active drug components may be combined with any oral non-toxic pharmaceutically acceptable inert carrier such as ethanol and the like. Moreover, when desired or necessary, suitable binders, lubricants, disintegrating agents and coloring agents can also be incorporated in the mixture. Suitable binders include starch, gelatin, natural sugars, corn sweeteners, natural and synthetic gums such as acacia, sodium alignate, carboxymethylcellulose, polyethylene glycol, and waxes. Lubricants for use in these dosage forms include boric acid, sodium benzoate, sodium acetate, sodium chloride, and the like. Disintegrators include, without limitation, starch, methylcellulose, agar, bentonite, guar gum, and the like.

The compounds of this invention exhibit antihypertensive activity as determined in the unanesthetized spontaneously hypertensive rat (SHR) assay and/or exhibit calcium ion antagonism as demonstrated in isolated thoracic aorta segments from male spontaneously hypertensive rats.

The test procedures employed to measure the antihypertensive and/or calcium antagonist activity of the compounds of the present invention are described below.

ANTI-HYPERTENSIVE ACTIVITY

Male, unanesthetized spontaneously hypertensive rats, 11 to 16 weeks old were used in this test procedure. The compounds to be tested were administered intragastrically at a dose of 50 mg/kg or intraarterially/intravenously at a dose of 10 mg/kg.

Initial mean arterial blood pressure was measured directly via a previously implanted arterial catheter immediately before administration of the test compound. Blood pressure readings were made at 1, 2, 3, and 4 hours following intragastric administration and at 5, 10, and 15 minutes following intraarterial or intravenous administration of the test compound. A compound was rated active if the mean post treatment blood pressure of treated rats was significantly different (p less than or equal to 0.05) than that of the control group concurrently administered placebo. Statistical comparisons were made using the paired Student's t test with two sided probability calculations.

The spontaneously hypertensive rat exhibits a genetically-linked hypertension that is similar in most respects to essential hypertension in man. Guanethidine, hydralazine, methyldopa, clonidine hydrochloride and captopril are active in the foregoing hypertensive rat assay and are clinically useful antihypertensive agents.

CALCIUM ANTAGONISM IN VASCULAR SMOOTH MUSCLE

Isolated thoracic aorta segments from the male spontaneously hypertensive rat were utilized in this test procedure.

The excised aorta segment was mounted in a tissue bath containing modified Krebs solution. After depolarization of the tissue with potassium salts (100 mM $K^+$), calcium chloride (in cumulative concentrations of $1 \times 10^{-3}M$, $3.2 \times 10^{-3}M$, and $1 \times 10^{-2}M$) was injected into the bath to produce vascular smooth muscle contraction. The developed tension (in grams) is measured and control dose-response values obtained. After one hour of incubation with a test compound at $1 \times 10^{-6}M$ concentration, the same doses of calcium ions were repeated. The log dose-response curves of the control and after treatment were analyzed by linear regression. The $pA_2$ value was calculated as a measure of calcium antagonism of the test compound. See J. H. Sanner and C. M. Prusa, *Life Sciences*, 27, 2565–2570 (1980); J. M. Van Rossum, *Arch. Int. Pharmacodyn.*, 143, 299–330, 1963. A compound was considered active as a vascular calcium antagonist if the $pA_2$ is 6.0 or greater.

Calcium ions play an essential role in induction and maintenance of vascular smooth muscle contractility. In potassium depolarized vascular smooth muscle, calcium antagonists may block the entry of calcium ions into the cell or act by other mechanisms to inhibit the contractions induced by calcium ions. The inhibition of calcium ion—induced contraction of vascular smooth muscle is used to test compounds for vascular calcium antagonism. Cardiovascular diseases such as arrhythmias, angina-pectoris, hypertension, and peripheral vascular disease may be causally related to abnormalities in cellular handling of calcium ions. Calcium antagonists/entry blockers have been proven to be of value in the treatment of the aforementioned cardiovascular diseases or conditions. Verapamil, nifedipine, diltiazem and other drugs are active in the foregoing test and have, likewise, been demonstrated to be clinically useful cardiovascular agents.

The compounds of the present invention are antihypertensive agents which advantageously have not been found to produce tachycardia or tachyphylaxis at test doses and the avoidance or minimization of such adverse side effects is clearly significant with respect to the ultimate usefulness of the present compounds as cardiovascular agents.

Reduction in arterial blood pressure is effected by decreasing total peripheral resistance as a result of arteriolar vasodilation produced by antagonism of calcium ions at the arterioles. Certain of the preferred compounds of the present invention also block the uptake of calcium ions into cultured vascular smooth muscle cells and antagonize the binding of nitrendipine to the calcium receptor in cardiac membranes.

The following non-limiting examples further illustrate details for the preparation of the compounds of the present invention. Those skilled in the art will readily understand that known variations of the conditions and processes of the following preparative procedures can be used to prepare these compounds. All temperatures are degrees Celsius unless otherwise noted.

EXAMPLE 1

Diethyl [[4-[[4-(2-methoxyphenyl)-1-piperazinyl]methyl]-phenyl]methyl]phosphonate, monohydrochloride

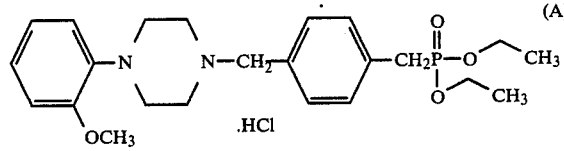

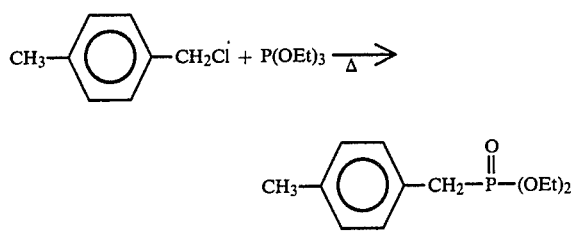

A mixture of α-chloro-p-xylene (104 g, 0.74 mole) and triethyl phosphite (123 g, 0.74 mole) was heated in an oil bath to ≃170° C. at which point refluxing began. It was then heated from 170°–220° C. for 2 hours and cooled to room temperature. Following distillation, the reaction mixture yielded 126.13 g (70%) of clear liquid.

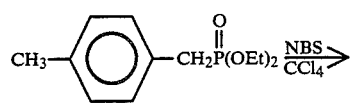

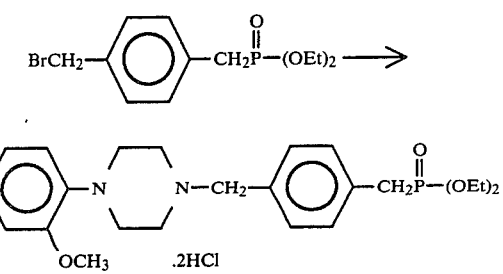

A mixture of the phosphate ester from step A (22.5 g, 0.093 mole), N-bromo succinimide (19.8 g, 0.111 mole) and benzoyl peroxide (50 mg) in 225 mL of CCl₄ was heated with a sunlamp until the solution began to reflux. Heating was continued off and on for a few minutes until the refluxing subsided. The reaction mixture was then heated at reflux for 15 minutes, cooled to room temperature, filtered and evaporated to dryness. The resulting oil was dissolved in ether/Skelly B, washed with brine and dried over MgSO₄. Removal of the solvent yielded 29.8 g of yellow oil.

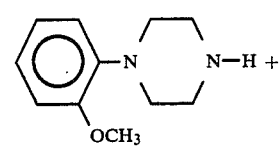

A mixture of 1-(o-methoxyphenyl)-piperazine (2.5 g, 0.013 mole), the phosphate ester from step B (4.2 g, 0.013 mole) and powdered K₂CO₃ (1.8 g, 0.013 mole) in 20 mL of DMF was stirred overnight at room temperature.

The reaction mixture was diluted with water and extracted 3×with ether. The combined ether layers were washed 2×with water, once with 1% NaOH and 2×with water and dried over MgSO₄. Removal of the solvent gave 4.7 g of yellow oil. Following chromatographic purification and conversion to the hydrochloride salt, the title product was obtained: mp. 146°–148° C. (dec).

Calc'd. for $C_{23}H_{33}N_2O_4P$ (0.2HCl salt): C, 54.59; H, 6.72; N, 5.54. Found: C, 54.56; H, 6.74; N, 5.57.

EXAMPLE 2

Diethyl [[4-[[4-(2-methylphenyl)-1-piperazinyl]methyl]]phenyl]-methyl]phosphonate, monohydrochloride

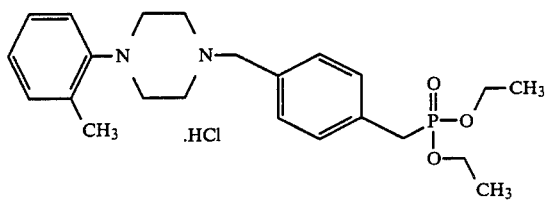

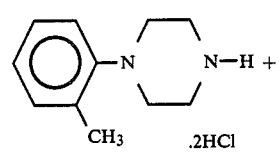

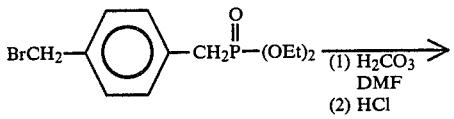

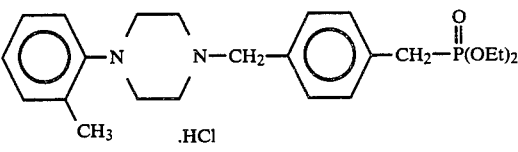

A mixture of o-tolyl-piperazine.2HCl (3.24 g, 0.013 mole), the phosphonate ester prepared according to Example 1B (4.2 g, 0.013 mole) and powdered K₂CO₃ (5.4 g, 0.039 mole) in 30 mL of DMF was stirred at room temperature overnight.

The reaction mixture was diluted with water and extracted 3× with ether. The combined organic layers were washed 1× with water, 1× with 1% NaOH and 1× with water and dried over MgSO₄. Removal of the solvent gave 5.2 g of yellow oil. Following chromatographic purification and conversion to the hydrochloride salt, the title product was obtained as a white solid: mp 171°–172° C. (dec).

Calc'd for $C_{23}H_{33}N_2O_3P$ (HCl salt): C, 60.99; H, 7.57; N, 6.18; Cl, 7.82. Found: C, 60.47; H, 7.17; N, 6.43; Cl, 7.77.

Utilizing reaction schemes I, II or III and appropriate starting materials and conditions as exemplified in the specific procedures detailed in Examples 1 and 2, the compounds set forth in Table I below were prepared.

TABLE I

| Example No. | Calc. For | Found | M.P. (°C.) |
|---|---|---|---|
| 3. diethyl [[4-[[4-(4-methoxyphenyl)-1-piperazinyl]methyl]phenyl]methyl]phosphonate, monohydrochloride, monohydrate .HCl.H₂O | C, 58.91<br>H, 7.31<br>N, 5.97<br>Cl, 7.56 | C, 59.01<br>H, 7.17<br>N, 6.00<br>Cl, 7.51 | 188–188.5 (dec) |
| 4. diethyl [[4-[[4-(4-chlorophenyl)-1-piperazinyl]methyl]phenyl]methyl]phosphonate, monohydrochloride .HCl | C, 55.82<br>H, 6.60<br>N, 5.92<br>Cl, 14.98 | C, 55.67<br>H, 6.50<br>N, 5.88<br>Cl, 15.12 | 210–211 (dec) |
| 5. diethyl [[4-[(4-phenyl-1-piperazinyl)methyl]phenyl]methyl]phosphonate, monohydrochloride .HCl | C, 60.20<br>H, 7.35<br>N, 6.38<br>Cl, 8.08 | C, 60.09<br>H, 7.39<br>N, 6.42<br>Cl, 8.02 | 197–198 (dec) |
| 6. diethyl [[4-[[4-(2-chlorophenyl)-1-piperazinyl]methyl]phenyl]methyl]phosphonate, monohydrochloride .HCl | C, 55.82<br>H, 6.60<br>N, 5.92<br>Cl, 14.98 | C, 55.40<br>H, 6.39<br>N, 5.96<br>Cl, 14.41 | 152–153 (dec) |
| 7. diethyl [[2-[[4-(2-methoxyphenyl)-1-piperazinyl] .HCl.H₂O | C, 56.12<br>H, 7.45<br>N, 5.75<br>Cl, 7.28 | C, 56.40<br>H, 6.90<br>N, 5.84<br>Cl, 7.69 | 67–75 |

TABLE I-continued

| Example No. | Calc. For | Found | M.P. (°C.) |
|---|---|---|---|
| methyl]phenyl]methyl]phosphonate, monohydrochloride, monohydrate | | | |
| 8. 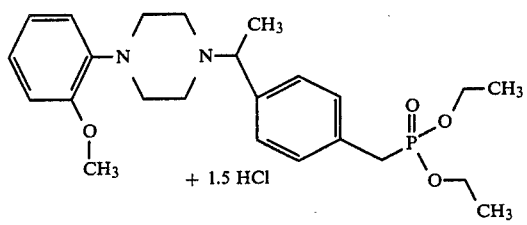 + 1.5 HCl  diethyl [[4-[1-[4-(2-methoxyphenyl)-1-piperazinyl]ethyl]phenyl]methyl]phosphonate, hydrochloride (2:3) | C, 57.51<br>H, 7.34<br>N, 5.59<br>Cl, 10.61 | C, 57.62<br>H, 7.10<br>N, 5.80<br>Cl, 9.18 | 60–70<br>Phase<br>Change to<br>Viscous<br>Oil |
| 9. 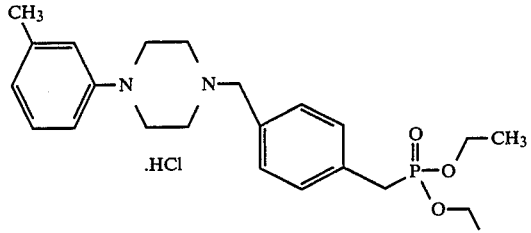 .HCl  diethyl [[4-[[4-(3-methylphenyl)-1-piperazinyl]methyl]phenyl]methyl]phosphonate, monohydrochloride | C, 60.99<br>H, 7.57<br>N, 6.18<br>Cl, 7.83 | C, 60.76<br>H, 7.43<br>N, 5.84<br>Cl, 8.10 | 187–188<br>(dec) |
| 10. 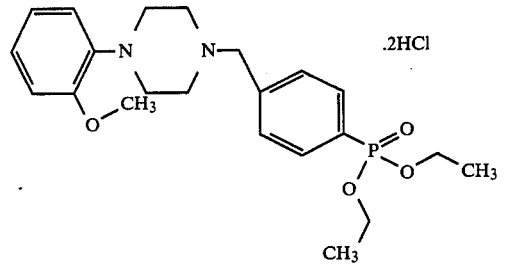 .2HCl  diethyl [4-[[4-(2-methoxyphenyl)-1-piperazinyl]methyl]phenyl]phosphonate, dihydrochloride | C, 53.77<br>H, 6.77<br>N, 5.70<br>Cl, 14.43 | C, 54.03<br>H, 6.61<br>N, 5.90<br>Cl, 13.37 | 144–148<br>(dec) |
| 11. 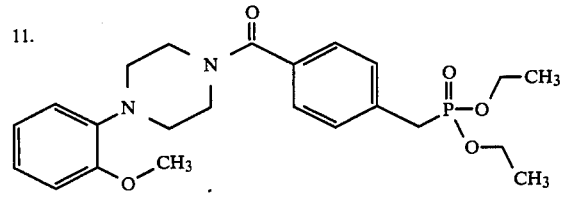 + 1.85 H$_2$SO$_4$  diethyl [[4-[[4-(2-methoxyphenyl)-1-piperazinyl]carbonyl]phenyl]methyl]phosphonate, sulfate | C, 44.00<br>H, 5.57<br>N, 4.46<br>S, 9.45 | C, 44.298<br>H, 5.60<br>N, 4.44<br>S, 9.87 | 176–186<br>(dec.) |
| 12. 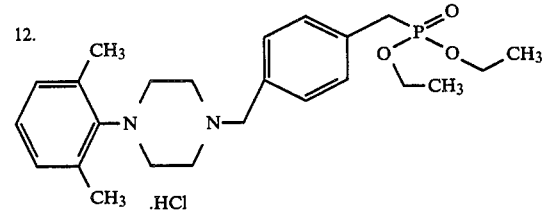 .HCl  diethyl [[4-[[4-(2,6-dimethylphenyl)-1-piperazinyl]methyl]phenyl]methyl]phosphonate, monohydrochloride | C, 61.72<br>H, 7.55<br>N, 6.00 | C, 61.94<br>H, 7.77<br>N, 6.29 | 176–179 |

TABLE I-continued

| Example No. | Calc. For | Found | M.P. (°C.) |
|---|---|---|---|
| 13. 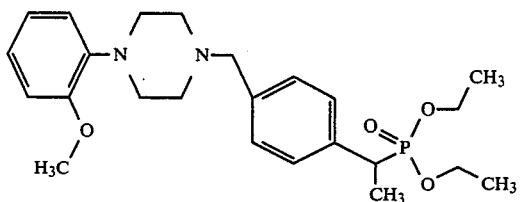<br>diethyl [1[4-[[4-(2-methoxyphenyl)-1-piperazinyl]methyl]phenyl]ethyl]phosphonate, hydrochloride (2:3) | C, 56.58<br>H, 7.27<br>N, 5.50<br>Cl, 10.44 | C, 56.92<br>H, 7.11<br>N, 5.54<br>Cl, 10.65 | 119–126<br>(dec.) |
| 14. 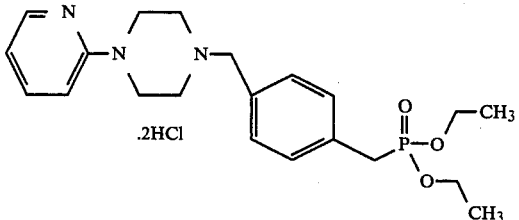<br>diethyl [[4-[[4-(2-pyridinyl)-1-piperazinyl]methyl]phenyl]methyl]phosphonate, dihydrochloride | C, 52.95<br>H, 6.77<br>N, 8.82 | C, 53.13<br>H, 7.06<br>N, 8.67 | 115–120 |

The results observed with respect to certain of the preferred compounds of the invention in the unanesthetized spontaneously hypertensive rat (SHR) assay previously described are set forth in Table II below.

TABLE II

| Compound Example No. | SHR (-mm Hg) @ 10 mg/kg intraveneous |
|---|---|
| 1 | −92.5 |
| 2 | −89.8 |
| 3 | −40.3 |
| 5 | −44.0 |
| 6 | −79.4 |
| 7 | −40.4 |
| 9 | −28.8 |
| 10 | −58.9 |
| 12 | −25.9 |
| 13 | −76.3 |
| 14 | −82.0 |

The calcium ion antagonist activities (pA₂ values) of the compounds of Examples 1, 10, 12 and 13 were 6.5, 6.6, 6.8 and 6.9, respectively, as measured in accordance with the assay previously described.

While the invention has been described and illustrated with reference to certain preferred embodiments thereof, those skilled in the art will appreciate that various changes, modifications and substitutions can be made therein without departing from the spirit of the invention. For example, effective dosages other than the preferred ranges set forth hereinabove may be applicable as a consequence of variations in the responsiveness of the mammal treated, severity of hypertension, dosage related adverse effects, if any, observed and analogous considerations. Likewise, the specific pharmacological responses observed may vary depending upon the particular active compounds selected or whether different active compounds are used in combination or in the presence of suitable pharmaceutical carriers, as well as the type of formulation and mode of administration employed, and such expected variations or differences in results are contemplated in accordance with the objects and practices of the present invention.

It is intended, therefore, that the invention be limited only by the scope of the claims which follow.

What is claimed is:

1. A compound of the formula

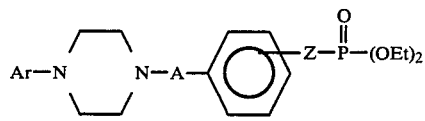

and the pharmaceutically acceptable salts thereof; wherein Ar is a pyridyl group or a

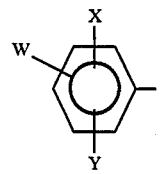

group, wherein X, Y and W are the same or different and independently selected from hydrogen, $C_1$–$C_4$ alkoxy, $C_1$–$C_6$ alkyl or halogen; wherein A represents —$CH_2$—,

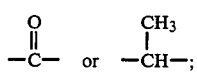

and wherein Z represents a bond or —$CH_2$— or

2. A compound according to claim 1 wherein said compound is of the formula

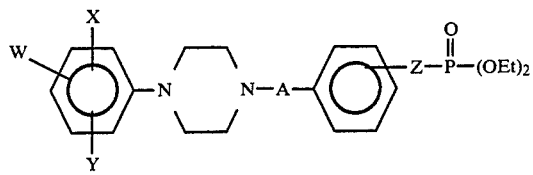

and the pharmaceutically acceptable salts thereof.

3. A compound according to claim 2 wherein two of X, Y or W are hydrogen and the other is $C_1$-$C_4$ alkoxy or $C_1$-$C_6$ alkyl.

4. A compound according to claim 2 wherein A is —$CH_2$—.

5. A compound according to claim 2 wherein Z represents —$CH_2$— or

6. A compound according to claim 2 wherein Z is —$CH_2$—.

7. A compound according to claim 2 wherein said compound is of the formula

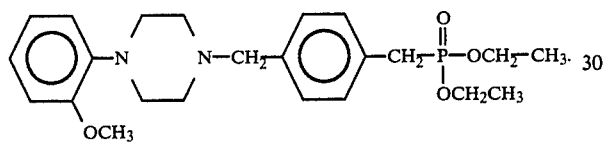

8. A compound according to claim 2 wherein said compound is of the formula

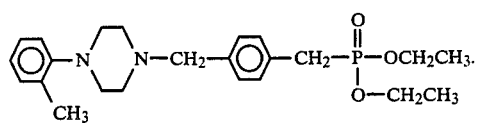

9. A compound according to claim 2 wherein said compound is of the formula

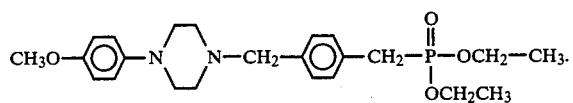

10. A compound according to claim 2 wherein said compound is of the formula

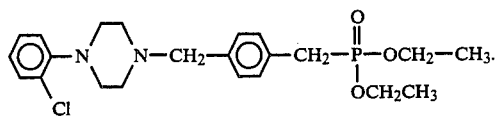

11. A compound according to claim 2 wherein said compound is of the formula

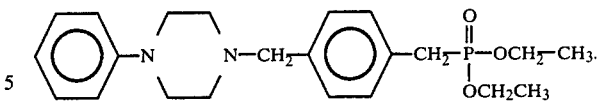

12. A compound according to claim 2 wherein said compound is of the formula

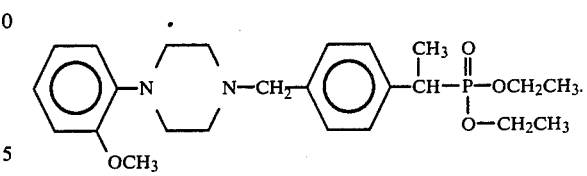

13. A compound according to claim 1 where Ar is pyridyl.

14. A compound according to claim 13 wherein said compound is of the formula

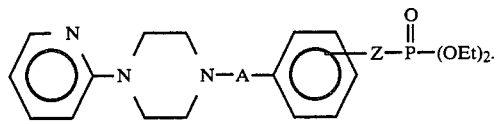

15. A compound according to claim 14 wherein said compound is of the formula

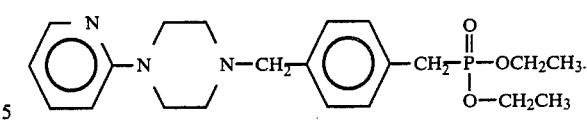

16. A pharmaceutical composition comprised of a pharmaceutical carrier in combination with a compound according to claim 1.

17. A composition according to claim 16 wherein said compound is of the formula

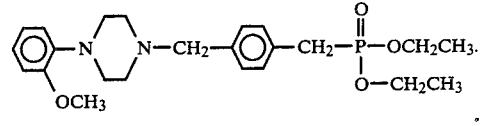

18. A method of promoting an antihypertensive effect in a mammal in need thereof comprising administering thereto an antihypertensively effetive amount of a compound according to claim 1.

19. A method according to claim 18 wherein said compound is of the formula

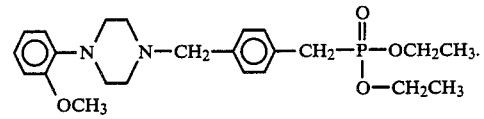

* * * * *